(12) United States Patent
Harthorn et al.

(10) Patent No.: US 6,904,818 B2
(45) Date of Patent: Jun. 14, 2005

(54) INTERNAL RISER INSPECTION DEVICE

(75) Inventors: Larry K. Harthorn, Carencro, LA (US); Pedro A. Dioquino, Fulshear, TX (US); Richard J. Milligan, Jr., Hourna, LA (US); Jason C. Good, Morgan City, LA (US); Neil D. Allen, Schreiver, LA (US); Richard D. Romero, Lafayette, LA (US)

(73) Assignee: Vetco Gray Inc., Houston, TX (US)

( * ) Notice: Subject to any disclaimer, the term of this patent is extended or adjusted under 35 U.S.C. 154(b) by 0 days.

(21) Appl. No.: 10/351,569

(22) Filed: Jan. 24, 2003

(65) Prior Publication Data

US 2003/0188589 A1 Oct. 9, 2003

Related U.S. Application Data

(60) Provisional application No. 60/370,444, filed on Apr. 5, 2002.

(51) Int. Cl.[7] .............................................. G01M 19/00
(52) U.S. Cl. .......................... 73/865.8; 73/640; 73/611; 73/622; 73/628; 73/601
(58) Field of Search .......................... 73/640, 611, 622, 73/628, 601, 865.8

(56) References Cited

U.S. PATENT DOCUMENTS

| | | | | |
|---|---|---|---|---|
| 3,455,150 | A | * | 7/1969 | Wood ........................ 73/640 |
| 3,810,384 | A | * | 5/1974 | Evans ........................ 73/611 |
| 3,868,847 | A | * | 3/1975 | Gunkel ...................... 73/622 |
| 3,888,114 | A | * | 6/1975 | Adams et al. ................ 73/628 |
| 3,943,756 | A | * | 3/1976 | Aubert et al. ................ 73/634 |
| 4,055,990 | A | * | 11/1977 | Topping ...................... 73/623 |
| 4,162,635 | A | * | 7/1979 | Triplett et al. ............... 73/623 |
| 4,213,345 | A | | 7/1980 | Dufour |
| 4,218,923 | A | * | 8/1980 | Triplett et al. ............... 73/623 |
| 4,285,242 | A | * | 8/1981 | Braithwaite .................. 73/623 |
| 4,285,243 | A | * | 8/1981 | Collingwood ................. 73/623 |
| 4,375,165 | A | | 3/1983 | De Sterke |
| 4,569,230 | A | * | 2/1986 | Asty et al. ................... 73/623 |
| 4,641,529 | A | * | 2/1987 | Lorenzi et al. ............... 73/601 |
| 4,663,727 | A | * | 5/1987 | Saporito et al. .............. 73/623 |
| 4,772,849 | A | | 9/1988 | Tedder |
| 4,876,672 | A | | 10/1989 | Petermann et al. |
| 4,964,059 | A | * | 10/1990 | Sugaya et al. ................ 73/598 |
| 5,097,710 | A | | 3/1992 | Palynchuk |
| 5,099,692 | A | | 3/1992 | Lodder et al. |
| 5,175,964 | A | | 1/1993 | Girndt |
| 5,285,689 | A | | 2/1994 | Hapstack et al. |
| 5,385,049 | A | | 1/1995 | Hunt et al. |
| 5,392,527 | A | | 2/1995 | Ziskovsky et al. |
| 5,454,267 | A | | 10/1995 | Moreau et al. |
| 5,574,223 | A | | 11/1996 | Kiefer |
| 5,587,534 | A | | 12/1996 | McColskey et al. |
| 5,661,241 | A | | 8/1997 | Harth, III et al. |
| 5,675,084 | A | | 10/1997 | Goedecke |
| 5,677,490 | A | * | 10/1997 | Gunther et al. ............... 73/622 |
| 5,770,800 | A | | 6/1998 | Jenkins et al. |
| 2002/0134178 | A1 | | 9/2002 | Knight et al. |

FOREIGN PATENT DOCUMENTS

WO  WO 02/44709  6/2002

* cited by examiner

Primary Examiner—Hezron Williams
Assistant Examiner—André K. Jackson
(74) Attorney, Agent, or Firm—Bracewell & Giuliani LLP (57) ABSTRACT

An internal inspection unit for pipe has ultrasonic transducers that inspect weld volume, weld root, and wall thickness. The ultrasonic transducers are mounted to a portion of the inspection unit that is rotatable, but no more than one full revolution. One of the units has independently movable shoes for each separate transducer. The shoes are moved between retracted and extended positions by pneumatic cylinders. The other unit has shoes that support more than one transducer, the shoes being biased outwardly by springs.

27 Claims, 7 Drawing Sheets

INTERNAL RISER INSPECTION DEVICE

This application claims the provisional application filing date of Apr. 5, 2002, Ser. No. 60/370,444 entitled "Internal Riser Inspection Device."

FIELD OF THE INVENTION

The invention relates in general to non-destructive testing of pipe, and in particular to a test unit that is conveyed internally through pipe for ultrasonically inspecting the pipe wall thickness and welds.

BACKGROUND OF THE INVENTION

Non-destructive testing of pipe has been done for many years utilizing ultrasonic transducers, eddy current measurements, x-ray and other techniques. Operators using pulse echo techniques with ultrasonic transducers can determine wall thickness, which is a measure of any corrosion that has occurred. For welds, operators have used flight diffraction ("TOFD") techniques with ultrasonic transducers. Also, a method known as pulse echo shear wave has been combined with TOFD transducer measurements to inspect portions of the weld that are missed by the TOFD transducer.

One type of pipe that requires periodic inspection is a drilling riser. Drilling risers, which are utilized for offshore drilling, extend from the drilling rig to a blowout preventer and lower marine riser package, which connect to a subsea wellhead. Drilling risers are made up of sections bolted together with flanges, each section being typically from 60–90 feet in length. Each drilling riser section has a central riser pipe that is normally about 18–24 inches in diameter. Several auxiliary lines are mounted to the exterior of the central riser pipe, the auxiliary lines being used for a choke, kill and hydraulic boost purposes. The auxiliary lines are smaller in diameter and mounted parallel and offset to the axis of the central riser pipe. Normally there will be at least one weld within each riser section, this being a center weld that connects two tubular pipes together to form the riser section. Also, normally the flange connectors are mounted to the ends of the riser sections by welding. Many risers also have buoyant jackets mounted to the exterior.

A drilling vessel may have several thousand feet of riser pipe, depending on the depth to which it is rated. During use, drill pipe with drill bits on the end, casing, and other well tools are lowered through the riser. Drilling mud returns up the riser. The auxiliary lines are pressurized for various purposes from time to time. The drilling riser is re-used after each well. Consequently it is necessary to periodically inspect the riser to make sure that it has no weaknesses that could result in leakage.

Inspection in the past has been done primarily by transporting the riser sections to a facility on land that performs the inspection services. The facility removes the buoyancy jackets and auxiliary lines from each section. The riser sections are cleaned and inspected from the exterior with various ultrasonic transducers. If the riser is coated with an epoxy, it must be removed at each inspection site. After inspection, the riser sections are reassembled and shipped back to the drilling vessel.

The transport of the riser sections to a testing facility on land is expensive. Also, it is time consuming to transport, clean, disassemble, inspect and reassemble the riser sections. During this time, unless a spare drilling riser can be obtained, the drilling rig would not be able to operate. Drilling rigs are very costly on a daily basis.

It has been proposed to inspect the drilling risers at the drilling vessel. Many drilling vessels have the ability to stack the riser sections horizontally on the vessel while not in use. However, there are a number of problems in doing so. The interior of the drilling riser is often not very clean, and may be coated with dried drilling mud. The central riser pipe is often out of round in portions. The welded areas of the central pipe may be misaligned slightly. Also, there is normally not much access room on the drilling rig at the ends of each riser section for staging the equipment necessary to do the inspection.

SUMMARY OF THE INVENTION

In this invention, tools are provided for inspecting riser pipe sections from the interior. A first ultrasonic transducer is mounted to an inspection unit for determining wall thickness of a pipe, and second and third ultrasonic transducers are mounted to the inspection unit for inspecting weld volume defects. The inspection unit is inserted into the pipe and conveyed along the pipe. Periodically, the first ultrasonic emits an acoustical signal into the pipe perpendicular to the pipe axis and detects a return acoustical signal from the pipe to determine wall thickness, which is an indication of corrosion.

For inspecting welds, the unit is placed in a position that positions the second and third ultrasonic transducers on opposite sides of the weld. The second transducer is caused to emit an acoustical signal into the weld, the reflection of which is detected by the third transducer to determine if a volume of the weld has any defects.

Preferably, the inspection unit has fourth and fifth ultrasonic transducers for inspecting a root of a weld, which is an area that the second and third ultrasonic transducers miss. The fourth and fifth transducers are placed on opposite sides of the weld simultaneously with the second and third ultrasonic transducers. Each of these is a pulse echo shear wave transducer oriented at an acute angle relative to the pipe axis. Each transducer emits a signal that reflects from the exterior surface of the pipe back inward through a root of the weld. After passing through the root, the reflected signal reflects back outwardly. If there are no defects, the pulse echo shear wave transducers do not receive any reflected signals. If a defect is present, the reflected signal is diffracted and received by the pulse echo shear wave transducer.

The inspection unit rotates while inspecting the welds. Preferably, a coupling liquid, such as water, is fed through a line to a cavity between each transducer and the wall of the pipe. In the embodiments shown, the inspection unit also rotates less than one turn while performing the wall thickness inspections. The inspection unit is programmed to collect data of the wall thickness at selected azimuth increments during the rotation.

Each of the transducers for the central pipe inspection device is mounted to a separate independently movable shoe. The inspection device preferably utilizes pneumatic cylinders to urge the shoes into contact with the inner diameter of the large diameter pipe. The operator can selectively move the transducers from retracted to extended positions. To save on shoe wear, the pulse echo transducers can be retracted while performing the weld inspections with the TOFD transducers and pulse echo shear wave transducers. Similarly, the TOFD transducers and pulse echo shear wave transducers can be retracted while performing the wall thickness inspection.

For the auxiliary lines, a smaller diameter unit is utilized. In this unit, multiple shoes are employed, but more than one transducer may be mounted to each shoe. The shoe is spring biased rather that urged by a pneumatic cylinder.

DESCRIPTION OF THE PREFERRED EMBODIMENT

Figure 1:
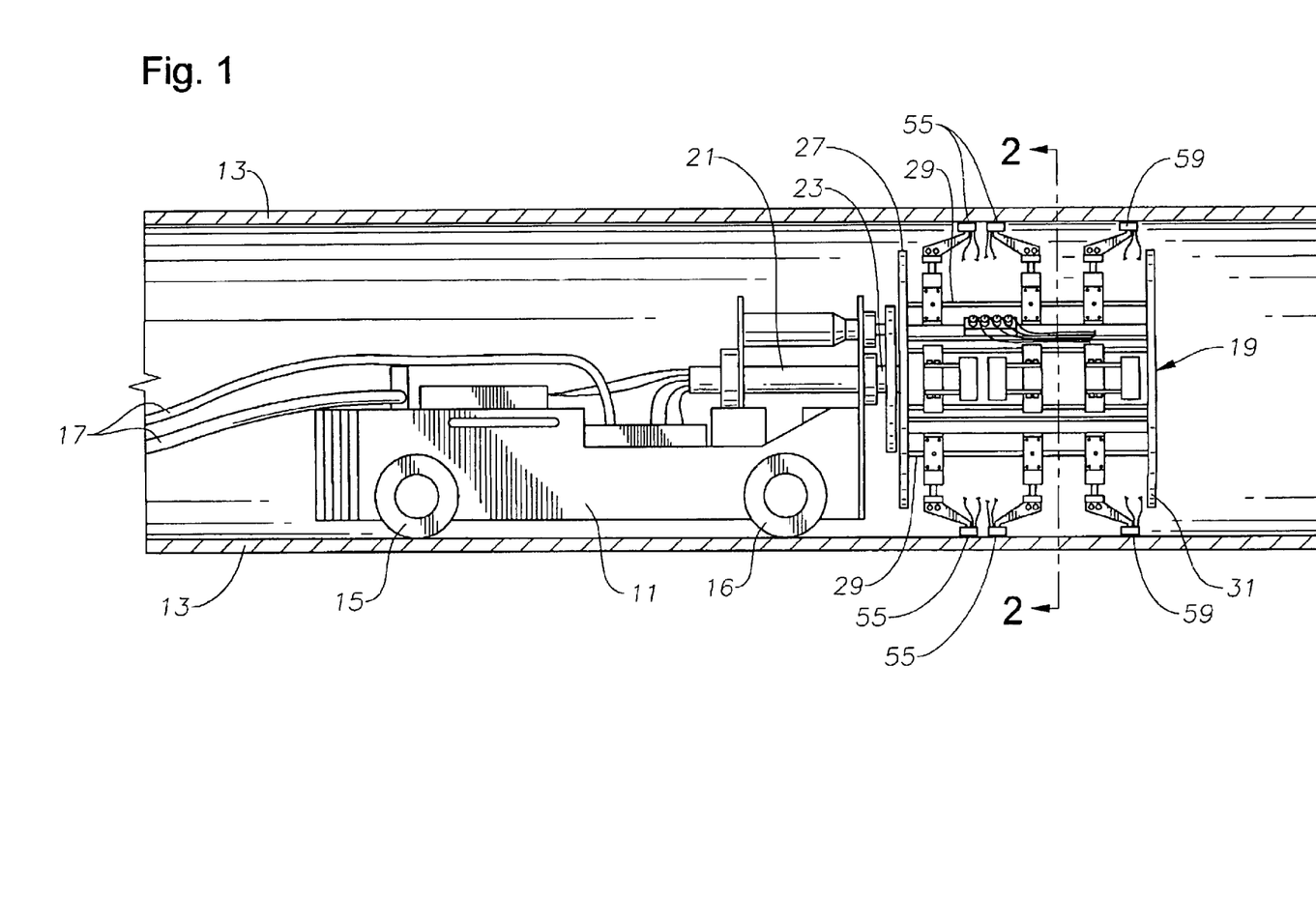
FIG. 1 is a cross-sectional view of an internal inspection device located inside a central pipe of a riser, the inspection device being constructed in accordance with this invention.

The inspection device of FIG. 1 has a self-propelled drive unit 11, which is shown within a central pipe 13 of a riser section. Drive unit 11 has two drive wheels 15 and two support wheels 16, which are spaced axially from drive wheels 15. Drive unit 11 is controlled and supplied with water by a plurality of lines 17 that extend out the end of pipe 13. The operator has controls for causing drive unit 11 to move forward and backward by providing signals through some of the lines 17.

The operator also has an odometer display that displays an indication of the linear distance that drive unit 11 is located from a zero point at the end of riser section 13. Encoder 18 (FIG. 5), which is mounted to the axle of support wheels 16, provides this information. Encoder 18 is preferably a conventional unit that uses a light beam that passes through a large number of apertures formed in a disc, the disc rotating with support wheels 16. Support wheels 16 are not driven, rather they freewheel. Consequently, any slippage that might occur in drive wheels 15 does not erroneously affect the odometer information provided to the operator.

Drive unit 11 has a linear motor 20 (FIG. 6) and a rotational motor 21. Linear motor 20 causes rotation of drive wheels 15. Rotational motor 21 rotates a drive shaft 23 that extends parallel to the longitudinal axis of drive unit 11. Rotational motor 21 has a linkage that causes it to rotate drive shaft 23 an increment that is less than one revolution, then rotate it back the other direction. A rotational encoder 25 (FIG. 6) provides an azimuth indication to the operator of the precise angle of rotation of drive shaft 23 at all times.

An inspection unit 19 is mounted to the forward end of drive unit 11 on drive shaft 23 for rotation therewith. In this embodiment, inspection unit 19 is located forward of both sets of wheels 15, 16, thus is supported in cantilever fashion by drive unit 11. Inspection unit 19 includes a rearward disc 27 that is mounted to drive shaft 23. Support rods 29 extend from rearward disc 27 forwardly. Support rods 29 are parallel to each other and parallel to the axis of drive shaft 23. A forward disc 31 is located at the forward ends of support rods 29 parallel to disc 27. Although, not shown, a pair of video cameras is preferably mounted on the forward face of forward disc 31.

A plurality of transducer mounting blocks 33 (FIG. 3) are mounted to the support rods 29. Transducer mounting blocks 33 are mounted at selective points along the lengths of support rods 29, which extend through holes within them. Each transducer mounting block 33 comprises a pneumatic cylinder and piston for moving rods 35 radially inward and outward between retracted and extended positions. A transducer plate 37 is mounted to the outer ends of pneumatic cylinder rods 35 for carrying a transducer shoe 39. Each transducer shoe 39 has an outer face that curves in a convex form for mating with the inner diameter of the riser section 13 (FIG. 1). Transducer shoe 39 is a hard plastic material and can be readily replaced for different diameters of riser pipe 13.

Figure 3:
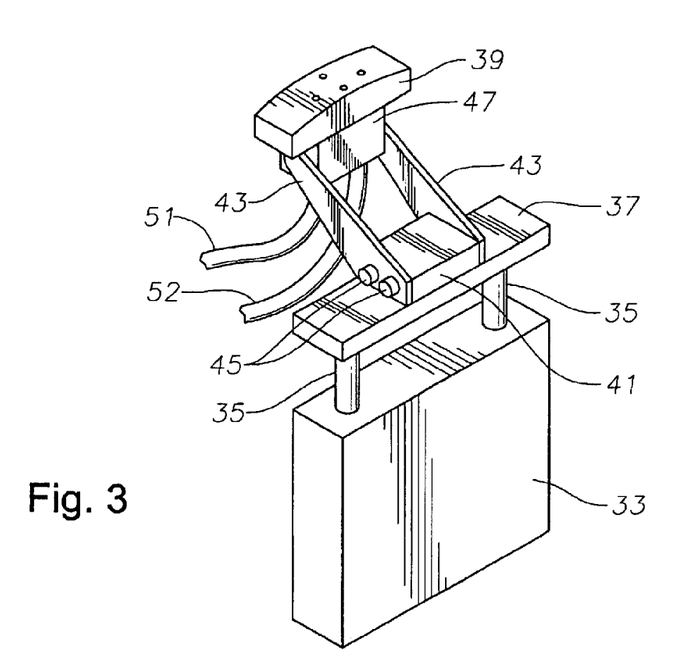
FIG. 3 is a perspective view of one of the transducer assemblies of the inspection device of FIG. 1.

A spacer block 41 supports each transducer shoe 39, each spacer block 41 being mounted to transducer plate 37 and a pair of braces 43. Braces 43 extend outward from drive shaft 23, but are angled relative to an axis passing through either of the pneumatic cylinder rods 35. Braces 43 are secured to spacer block 41 by fasteners 45.

Figure 4:
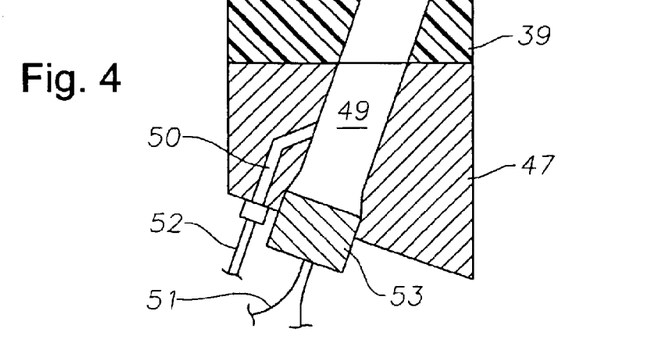
FIG. 4 is an enlarged cross-sectional view of part of one of the transducer assemblies of the inspection devise of FIG. 1.

Referring to FIG. 4, a recess or cavity 49 extends from the outer face of each transducer shoe 39 inward through transducer shoe 39 and upper spacer block 47. A small water passage 50 extends through upper spacer block 47 and into transducer shoe 39, where it joins cavity 49. A small flexible tube 52 joins water passage 50 for delivering water to cavity 49. A transducer 53 is mounted to the inward side of upper spacer block 47 at the base of cavity 49. Transducer 53 is a conventional piezoelectric device that will emit and/or receive acoustical signals. In this embodiment, each transducer shoe 39 has only one transducer 53. Wires 51 lead to transducer 53 to supply electrical energy to cause a sound pulse to be emitted. The transducers 53 used for pulse echo measurements convert acoustical reflected signals received into electrical energy, which is transmitted through one of the wires 51.

Figure 2:
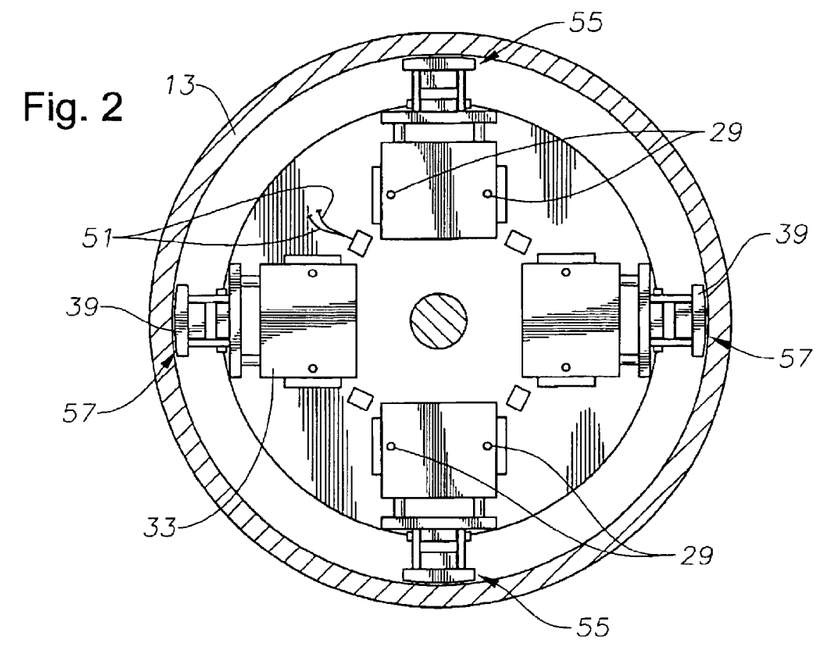
FIG. 2 is a cross-sectional view of the inspection device of FIG. 1, taken along the line 2—2 of FIG. 1.

Referring to FIGS. 1 and 2, inspection unit 19 preferably has two transducer pairs 55 for measuring weld volume by the TOFD method. The TOFD transducers 55 within each pair are spaced axially apart a selected distance, with one being more forward of the other. Each pair of TOFD transducers 55 is 180 degrees from the other pair of transducers 55. The forward transducer 55 in each pair is located in the same radial plane as the forward transducer 55 in the other pair. Similarly, the rearward transducer 55 in each pair is located the same axial position along inspection unit 19 as the rearward transducer of the pair located 180 degrees away.

Inspection unit 19 also has two transducer pairs 57 (FIG. 2) for measuring a root of a weld by pulse echo shear wave techniques, also referred to herein as shear wave. Each pair of transducers 57 is positioned the same axial distance as the forward and rearward TOFD transducers 55. Each transducer 57 is spaced a selected axial distance from the other transducer 57 of the pair. The pairs of shear wave transducers 57 are located 180 degrees apart from each other. FIG. 2 shows a pair of TOFD transducers 55 located at the zero degree position and another pair at the 180 degree positions, while shear wave transducers 57 are located at the 90 degree and 270 degree positions.

In this embodiment, inspection device 19 also has four transducers 59 that measure wall thickness, particularly utilizing pulse echo techniques. Pulse echo transducers 59 are located at the zero degree, 90 degree, 180 degree, and 270 degree positions. Pulse echo transducers 59 are located in the same radial plane, which is spaced forward of transducers 55 and 57 in this exemplary embodiment. Note that a different number of transducers than four could be utilized for pulse echo transducers 59 as well as for the other transducers 55, 57.

Figure 6:
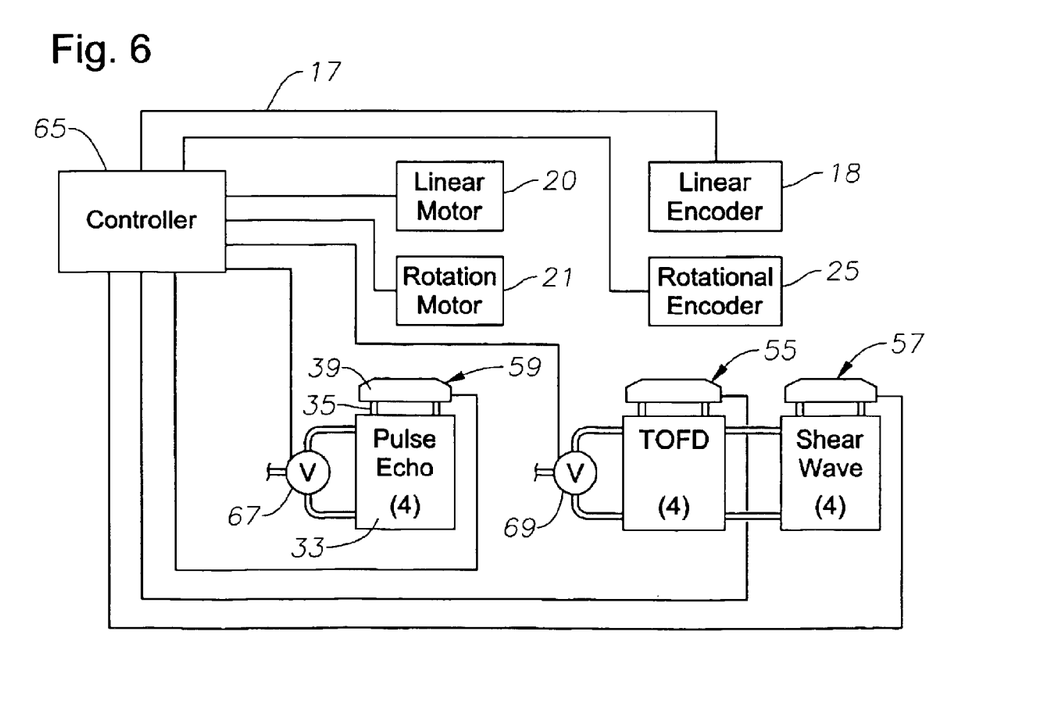
FIG. 6 is a schematic illustration of the various components of the inspection device of FIG. 1.

Referring to FIG. 6, a controller 65 is located exterior of riser section 13 for remotely controlling the inspection device through lines 17. Controller 65 includes a power supply, a computer, a monitor, a keyboard, and a joystick. Controller 65 also controls two pneumatic valves 67, 69. Valve 67 is connected to a supply of air pressure and will selectively cause the piston within mounting block 33 of each pulse echo transducer 59 to move between a retracted position and a radially outward extended position. Valve 67 causes the four pulse echo transducers 59 to move radially outward in unison or to retract in unison. Valve 69 independently controls the remaining transducers, these being TOFD transducers 55 and shear wave transducers 57. Valve 69 causes the four TOFD transducers 55 and the four shear wave transducers 57 to move between the retracted and extended positions in unison independent of pulse echo transducers 59.

Figure 7:
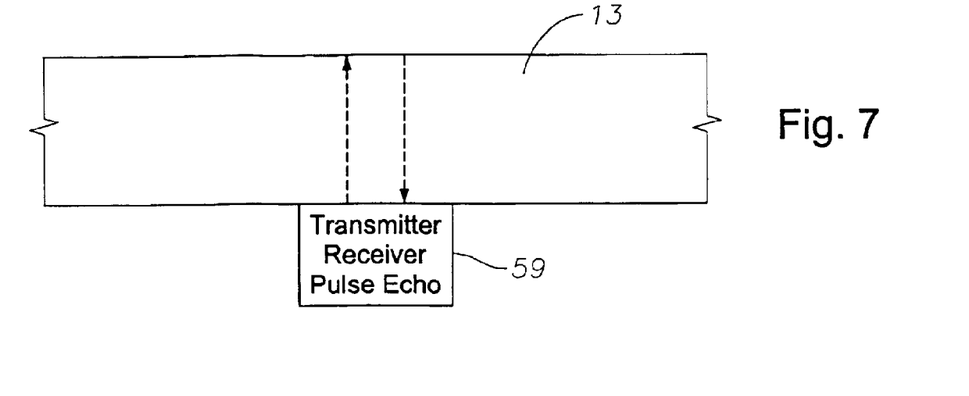
FIG. 7 is a cross-sectional view of a portion of the riser in FIG. 1, showing an ultrasonic transducer measuring wall thickness utilizing a pulse echo method.

Referring to FIG. 7, each pulse echo transducer 59 is of a type that transmits and receives. The shoe 39 (FIG. 3) that holds each transducer 59 is placed in contact with the inner diameter of riser section 13 with each pulse echo transducer 59 pointing radially outward, normal to the inner diameter of riser section 13. Water is delivered to cavity 49 (FIG. 4) to provide a liquid coupling. Each transducer 59 transmits an acoustic signal through the water, which communicates to riser section 13. The signal travels to the outer diameter of riser section 13, and is reflected back to the inner diameter of riser 13, where it is received by transducer 59. The reflected signal reverberates back and forth between the inner and outer diameters of riser section 13. The sound received by transducers 59 is converted into electrical signals, which are transmitted to controller 65 (FIG. 6). Controller 65 analyses them in a conventional manner. The thickness of riser section 13 is determined by measuring the time that it takes for the signal to return to the inner diameter of riser section 13.

Figure 8:
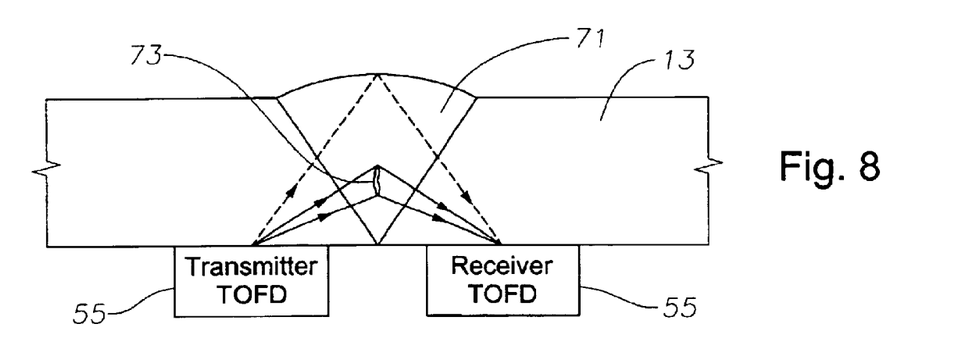
FIG. 8 is a cross-sectional view of a weld of the riser of FIG. 1, showing TOFD transducers inspecting for defects in the volume of the weld.

FIG. 8 illustrates the TOFD method, which is also known in the art. Within each pair, one of the TOFD transducers 55 is a transmitter and the other is a receiver. The receiver is spaced axially from the transmitter, either on the forward side or the rearward side of the transmitter. TOFD transducers 55 are positioned on both sides of and in close proximity to a weld 71. Weld 71 is a typical weld formed between two beveled ends of tubular members that make up riser section 13. Weld 71 has a triangular cross-section, with the apex or root of weld 71 being at the inner diameter and the cap at the outer diameter. The axial distance between the TOFD transducers 55 in each pair is greater than the width of the cap of weld 71. The TOFD transducers 55 are angled toward each other, so that the signal from the transmitter TOFD transducer 55 passes through the wall of riser section 13 at a selected angle, such as about 60 degrees and reflects to the receiver TOFD transducer 55.

Inspection unit 19 is rotated about drive shaft 23 (FIG. 1) while the transmitter TOFD transducer 55 emits sound pulses through the water coupling in cavities 49. The signals pass through the volume of weld 71 and reflect from the outer diameter of weld 71 to the receiver TOFD transducer 55. If weld 71 has a flaw 73, some of the signals will be diffracted at the tips of flaw 73. The diffracted signals are also received by the receiver TOFD transducer 55, as illustrated. The time that it takes for the sound waves to reach receiver TOFD transducer 55 is different for the diffracted pattern versus the non-diffracted pattern, and this difference is analyzed in a known manner to provide an indication of flaw 73.

Figure 9:
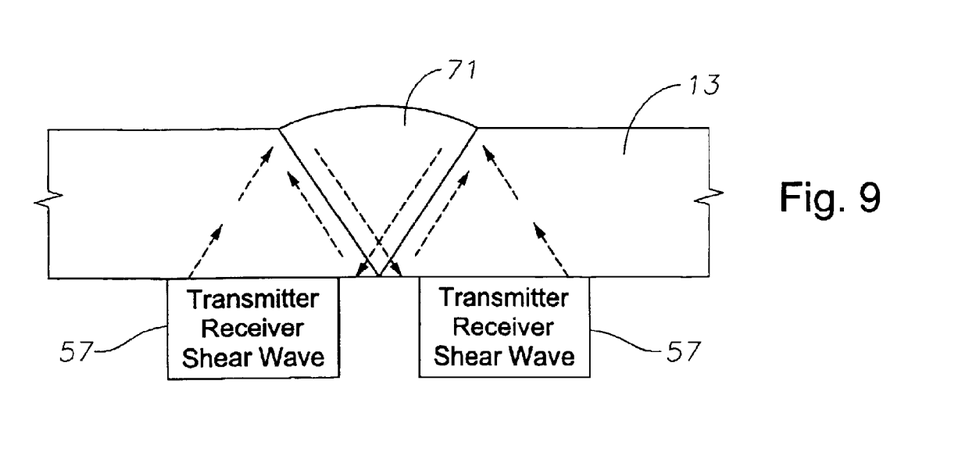
FIG. 9 is a schematic cross-sectional view of the weld of FIG. 8, showing pulse echo shear wave transducers inspecting for defects in the root of the weld.

The TOFD method measures the volume of the weld, which is all of the weld except for the root portion in the vicinity of the inner diameter. The pulse echo shear wave technique is employed, as illustrated in FIG. 9, to inspect for any flaws in the root portion of weld 71. Each shear wave transducer 57 is of a pulse echo type, having both a receiver and a transmitter. Each transducer 57 is angled toward the other in a manner similar to TOFD transducers 55 (FIG. 8). Shear wave transducers 57 are also axially spaced apart for positioning on opposite sides of weld 71 at approximately the same spacing as TOFD transducers 55. Each shear wave transducer 57 within each pair emits a sound pulse, but at a slightly different time from the other transducer 57 in the same pair so as to avoid interference with each other. Shear wave transducers 57 are oriented so that the sound waves are directed toward the outer side of riser section 13 near but not through the volume of weld 71. The angles are selected so that the sound pulse will contact the outer diameter of riser 13 and reflect back through the root of weld 71. If the root is free of any defects, the reflected signal contacts the inner diameter of riser section 13 between shear wave transducers 57 and reflects back outward. Because of the positioning of shear wave transducers 57, none of the shear wave transducers 57 will receive any reflected signals if the root is free of defects. However, if a flaw is encountered, diffraction will occur and one or both of the transducers 57 in each pair will receive a return signal that emanated from the other transducer 57. Controller 65 analyzes the return signal in a known manner to provide an indication to the operator.

In operation, the operator can inspect the wall thickness and welds 71 (FIG. 8) of riser 13 during one round trip pass through riser section 13. The inspection devise does not need to be pulled from riser section 13 between inspecting for corrosion with pulse echo transducers 59 and inspecting for weld defects with TOFD transducers 55 and shear wave transducers 57. In a preferred technique, the operator inspects all the welds 71 first, then inspects for corrosion. However, this could be reversed. Also, if desired, the operator could inspect a portion of riser section 13 for corrosion and inspect the welds 71 as they are encountered.

In the preferred technique, however, the operator first retracts all of the transducers 55, 57, 59 by controlling valves 67, 69 (FIG. 6). The operator inserts the device into one end of the riser section 13, which may be either the box end or the pin end. Once inserted, the operator advances drive unit 11 to a point that positions TOFD transducers 55 and shear wave transducers 57 on opposite sides of the first weld 71 (FIGS. 8 and 9). The operator stops the linear movement of unit 11 and moves shoes 39 containing transducers 55 and 57 outward by controlling valve 69 (FIG. 6). The operator causes water to flow to cavities 49 (FIG. 4) and actuates rotational motor 21 to rotate inspection unit 19. The entire inspection unit 19 will rotate while pulses are continually emitted by the various transducers 55, 57 and received by the respective transducers 55, 57. The operator receives signals from lines 17 and in the manner described above, analyzes weld 71 to determine for any defects.

Preferably, inspection unit 19 rotates only 180 degrees at each weld 71. Each pair of TOFD transducers 55 will sweep and measure 180 degrees, thus covering all 360 degrees of weld 71 during the 180 degree rotation. Similarly, each pair of shear wave transducers 57 will sweep 180 degrees. There is no need to rotate more than 180 degrees if the device has two pairs of TOFD transducers 55 and two pair of shear wave transducers 57. If the inspection device had only a single pair of TOFD transducers 55 and shear wave transducers 57, then it would be necessary to rotate inspection unit 19 one full revolution. Rotation more than one revolution is not needed and would twist lines leading to inspection unit 19 more than desired.

Figure 5:
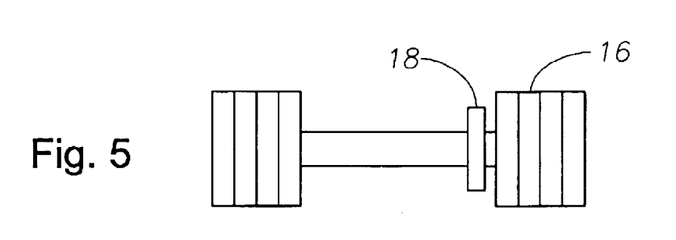
FIG. 5 is a schematic illustration of two of the wheels of the inspection device of FIG. 1, and showing an encoder.

Once the inspection of the first weld 71 is completed, the operator optionally retracts transducers 55, 57 to save wear on shoes 39 and actuates linear motor 20 to advance inspection unit 19 to the next weld 71. The operator will have a general indication of the position of the next weld 71 based on information provided and the odometer reading provided by encoder 18 (FIG. 5). Also, the video cameras provide a visual aid for the operator to properly position transducers 55 and 57 on opposite sides of the next weld 71. The operator optionally may leave inspection unit 19 in the 180 degree rotated position that existed at the conclusion of inspecting the first weld 71. At the next weld 71, the operator can inspect by rotating inspection unit 19 the opposite direction for 180 degrees. Once the operator reaches the opposite end, all of the welds 71, normally three, will have been inspected, with the data recorded in a memory storage unit of the controller 65 (FIG. 6).

The operator then may make wall thickness tests with the pulse echo transducers 59. Rather than bringing drive unit 11 back to the beginning end of riser section 13, it is more efficient to operate drive unit 11 in reverse and start making pulse echo measurements from the far end. The operator will be given instructions as to what lineal increments, or inspection areas, the wall thickness inspections are to be made. Also, the operator will be informed as to how many inspection sites are to be made around the circumference of riser section 13 at each inspection area or zone.

Referring to FIGS. 10–18, assume for example that the operator is to make pulse echo inspections at inspection areas one foot apart along the length of riser 13. Also, the operator may be instructed to have an inspection site every 45 degrees around the circumference at each inspection zone. In this embodiment, there are only four pulse echo transducers 59, each 90 degrees apart from the other. Consequently, the operator will provide instructions to controller 65 (FIG. 6) to collect data when rotational encoder 25 indicates that inspection unit 19 is in the zero degree rotational position, the 45 degree rotational position, and the 90 degree rotational position. Data is thus collected for inspection sites that are 45 degrees apart.

In the example of FIGS. 10–18, symbol 75 indicates the zero point for rotation of inspection unit 19 (FIG. 1). At the first inspection area, the operator actuates valve 67 to extend transducers 59 and valve 69 to retract transducers 55, 57, unless they have already been retracted. The operator takes the first measurement while symbol 75 is in the zero degree position, providing data for inspection sites at the zero degree, 90 degree, 180 degree, and 270 degree positions. The operator actuates rotational motor 21 (FIG. 1), which causes inspection unit 19 to rotate. Controller 65 causes signals to be recorded and computed when inspection unit 19 reaches the next inspection site at the first inspection area, which is the 45 degree rotational position illustrated in FIG. 11. Rotational encoder 25 provides the azimuth information to controller 65, which automatically causes the reading to occur at the 45 degree inspection site. At this point, all desired inspection sites at the first inspection area will have been made. In this embodiment, inspection unit 19 does not cease to rotate at the 45 degree inspection site, and will normally rotate a preprogrammed amount, such as 90 degrees. No additional reading, however, is taken in the position of FIG. 12. Also, sound pulses are continually emitted and received by transducers 59 during the full 90 degree rotation, but they are not recorded and computed by controller 65. Readings could be made at much shorter rotational increments, such as 5 degrees, with the amount of data storage of controller 65 being the limitation. Furthermore, inspection unit 19 could be rotated 180 degrees, if desired, but with four transducers 59, readings would be taken only during the first 90 degrees of rotation, regardless of the number of circumferentially-spaced inspection sites selected at each inspection zone.

Figure 10:
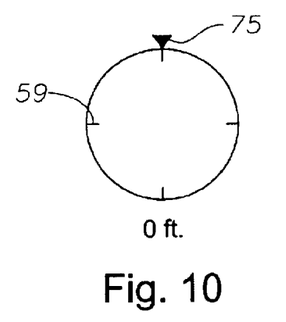
FIGS. 10–18 are schematic sequential illustrations of the rotational movement that the pulse echo transducers undergo at each inspection area along the riser pipe.
Figure 11:
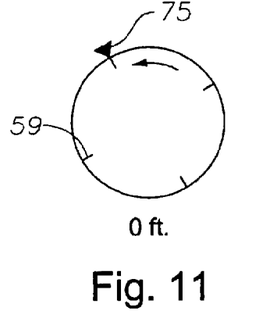
Figure 12:
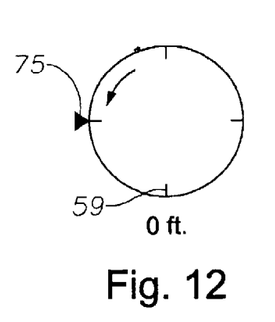
Figure 13:
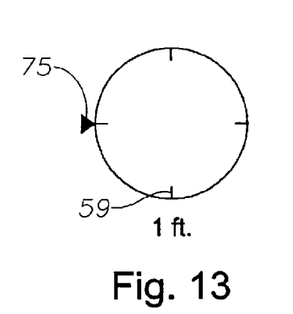
Figure 14:
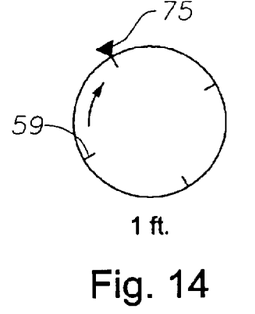
Figure 15:
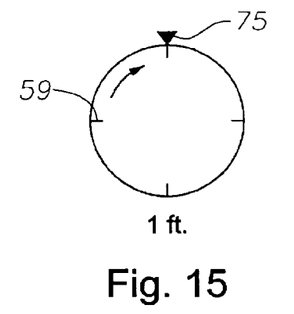
Figure 16:
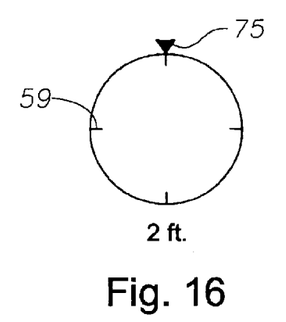
Figure 17:
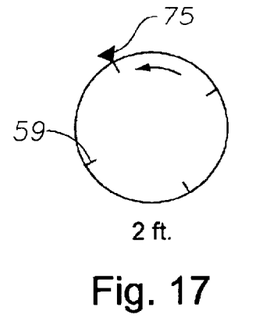
Figure 18:
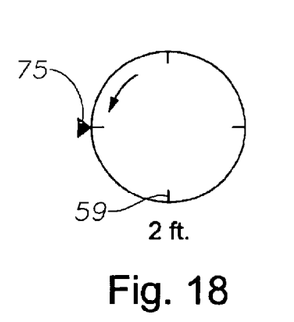

Once the rotation of inspection unit 19 is completed at the first inspection site of FIGS. 10–12, the operator moves to the next inspection site, which is shown in FIGS. 13–15, with the shoes for transducers 59 optionally retracted. The operator does not need to rotate inspection unit 19 back to the zero degree position of FIG. 10 prior to reaching the second inspection area. Rather, the operator can take readings simultaneously while causing inspection unit 19 to rotate in the reverse direction. Controller 65 is programmed to take readings at the desired azimuth increments during the 90 degree reverse rotation. At the conclusion of the 90 degree rotation at the one foot interval, shown in FIG. 15, the operator actuates linear motor 20 to move to the third inspection site, shown in FIGS. 16–18. The process is then repeated until the full length of riser section 13 has been inspected. At any time, the operator is free to reverse linear motor 20 and retake readings at any particular inspection area. If more pulse echo transducers 59 are utilized than four, it may not be necessary to rotate inspection unit 19 because adequate coverage could be obtained without rotation.

Figure 19:
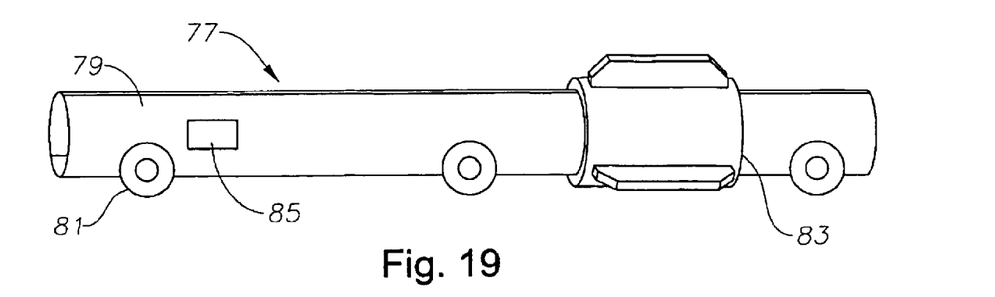
FIG. 19 is a perspective view of an inspection device in accordance with the invention for inspecting auxiliary lines of a drilling riser.
Figure 20A:
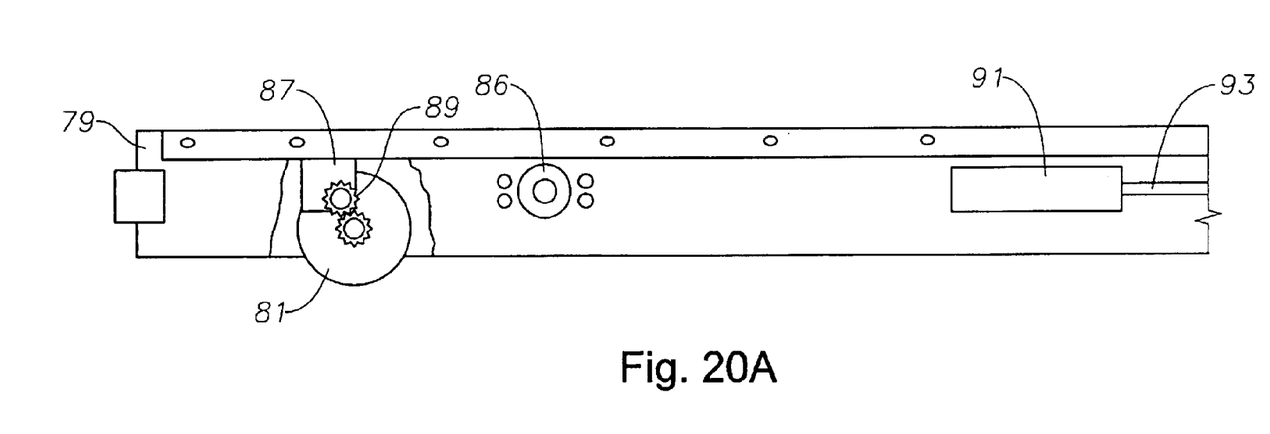
FIGS. 20a and 20b comprise a partially sectioned and exploded view of the inspection device of FIG. 19.
Figure 20B:
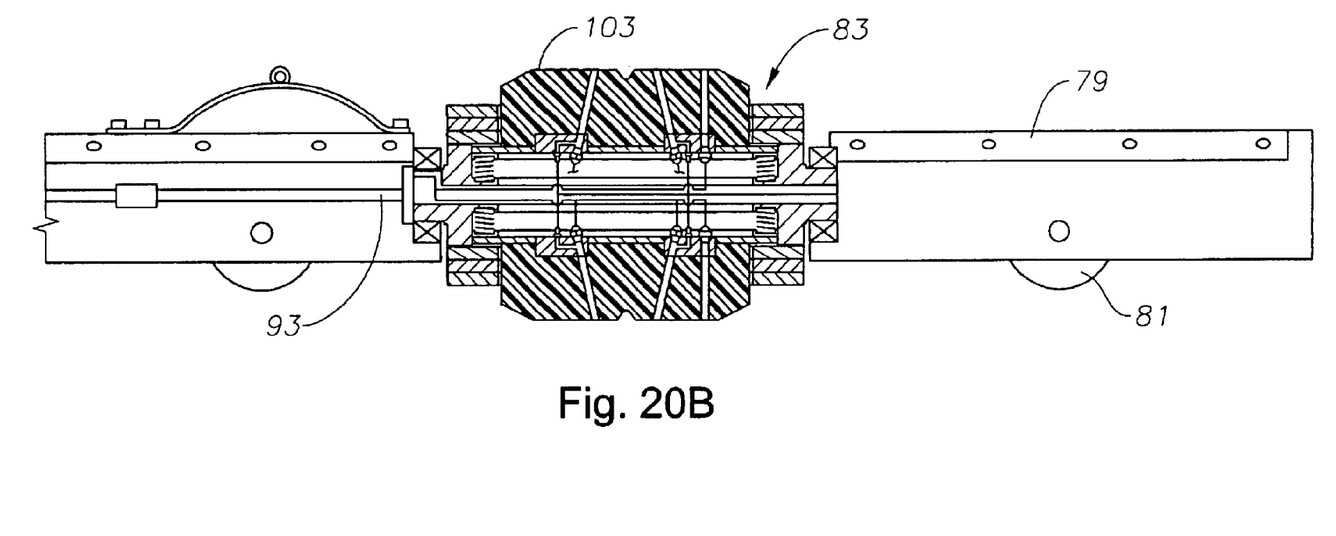
Figure 21:
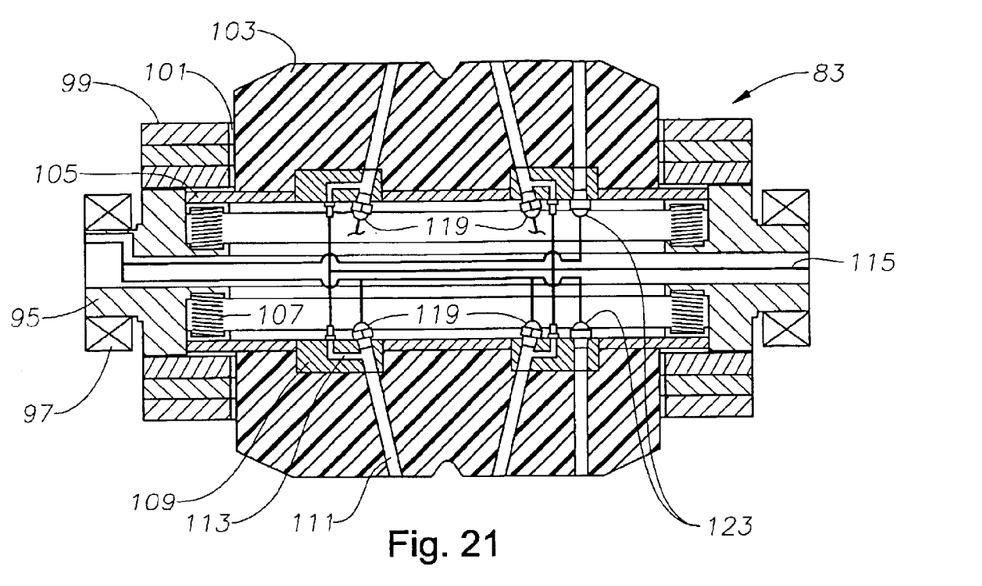
FIG. 21 is an enlarged sectional view of the inspection unit of the inspection device of FIG. 19.

FIGS. 19–21 disclose a small diameter unit 77 for inspecting the auxiliary lines (not shown) of riser section 13 (FIG. 1). The auxiliary lines of riser section 13 may remain in place mounted to the exterior of the riser section 13 during this inspection. As in the inspection of the central pipe section 13 (FIG. 1), this is preferably done while riser section 13 is horizontal and located at the offshore drilling rig. Unit 77 has an elongated tubular housing 79 supported on a plurality of wheels 81. In this exemplary embodiment, wheels 81 are not self-propelled, rather unit 77 is pulled through the auxiliary pipe by a cable. An inspection unit 83 is mounted to housing 79 between its ends. Inspection unit 83 is preferably mounted between two of the sets of wheels 81. Video camera ports 85 are located in housing 79 for providing visual access for a video camera 86 (FIG. 20A).

Small diameter unit 77 also has an odometer or encoder 87 mounted to the frame of housing 79. Encoder 87 is driven by a gear train 89, which in turn is driven by rotational movements of one of the sets of wheels 81. A rotational motor 91 is located in housing 79 for rotating a shaft 93 (FIG. 20b), which is parallel to the longitudal axis of small diameter unit 77. Shaft 93 extends into engagement with an axle 95 of inspection unit 83. As in the first embodiment, motor 91 preferably rotates inspection unit 83 180 degrees for measurements of welds, and 90 degrees for inspection of wall thickness. An azimuth encoder (no shown) provides an indication of the particular angular orientation of inspection unit 83 at all times.

As shown in FIG. 21, axle 95 is mounted on bearings 97 that allow the entire inspection unit 83 to rotate relative to housing 77 (FIG. 20A and 20B). A plurality of outer sleeves 99 are mounted to axle 95 for rotation therewith. Outer sleeves 99 have plurality of slots 101, which in this embodiment comprises four. A transducer shoe 103 extends from each slot 101. Each slot 101 is located 90 degrees from the other and is an elongated aperture parallel to the axis of axle 95. Transducer shoe 103 is a hard plastic member that is mounted on a plate 105. Plate 105 is urged outward by springs 107 located at each end. Springs 107 independently urge each transducer shoe 103 to a radial outward position.

Figure 22:
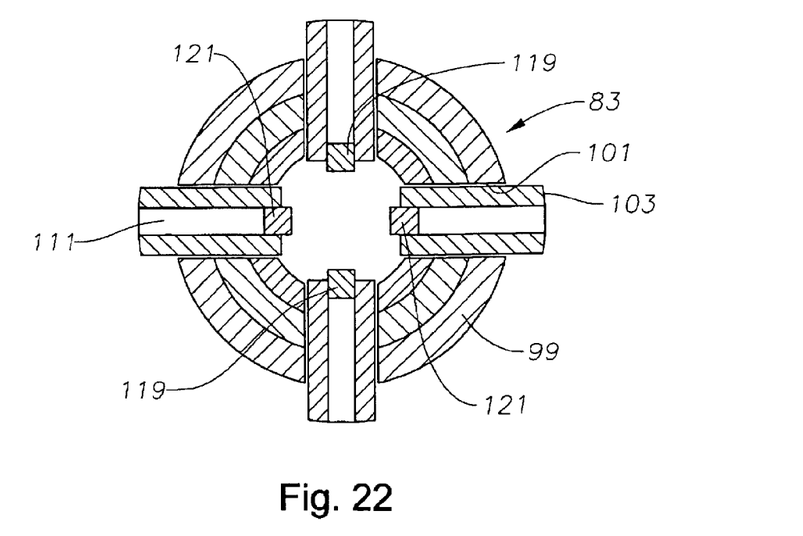
FIG. 22 is a sectional view of the inspection unit of FIG. 21, taken along the line 22-22 of FIG. 21.

A plurality of mounting blocks 109 are located within each transducer shoe 103. A plurality of cavities 111 extend through each transducer shoe 103 and mounting block 109. A water passage 113 leads to each cavity 111, water passage 113 being connected to a water conduit 115. TOFD transducers 119 are located in two of the shoes 103, with one pair of TOFD transducers 119 at the zero degree shoe 103 and the other at a 180 degree shoe 103 in FIG. 22. Similarly shear wave transducers 121 are mounted to shoes 103 at 90 degree and 270 degree positions. There are preferably four pulse echo transducers 123 spaced 90 degrees apart from each other.

Small diameter unit 77 operates in the same manner as the large diameter unit, except that it is pulled manually from inspection zone to inspection zone or weld to weld, and transducer shoes 103 do not retract. While inspecting a weld, motor 91 rotates inspection unit 83 180 degrees. Rotational motor 91 rotates inspection unit 83 90 degrees at each inspection area while inspecting wall thickness. During that interval, the controller will cause data points to be taken at the selected rotational increments.

The invention has significant advantages. It allows efficient inspection of riser pipe sections on a rig. This avoids transporting the riser pipe sections to land, stripping the buoyant members and auxiliary lines then inspecting the pipes from the exterior. Inspecting internally avoids problems encountered due to external coatings. Because of the coupling liquid, the interiors of the riser sections do not have to be spotlessly clean for inspection to be valid. The independently movable shoes accommodate for out-of-round pipe and misaligned welds. Performing the weld tests and the corrosion tests with the same unit reduces the amount of equipment required and also saves time in that it can be done during one trip through the riser section. Rotating the inspection unit less than one full turn allows the wires and tubes to be connected directly between the unit and the exterior without over twisting them. There is no need for electrical slip rings and rotational type manifolds.

While the invention has been shown in only two of its forms, it should be apparent to those skilled in the art that is it not so limited but is susceptible to various changes without departing from the scope of the invention. For example, although shown inspecting riser pipe while stored horizontally, with modifications, the inspection device could be utilized while the riser pipe is suspended vertically as well.

We claim:

1. A method of inspecting a pipe, comprising:
   (a) mounting an inspection unit to a frame and mounting to the inspection unit a first ultrasonic transducer for determining wall thickness of a pipe and second and third ultrasonic transducers axially spaced apart from each other relative to a longitudinal axis of the unit for inspecting weld volume defects;
   (b) inserting the unit with the first, second and third ultrasonic transducers mounted thereto into a pipe and conveying the unit along the pipe;
   (c) periodically causing the first ultrasonic transducer to emit an acoustical signal into a wall of the pipe and detecting a return acoustical signal from the pipe and thereby determining wall thickness of the pipe; and
   (d) positioning the unit in a position that places the second and third ultrasonic transducers on opposite sides of a weld that extends circumferentially around the pipe, then rotating the second and third ultrasonic transducers relative to the frame about the axis of the unit and simultaneously causing the second ultrasonic transducer to emit an acoustical signal into the weld and receiving a return acoustical signal with the third ultrasonic transducer, to determine if a volume of the weld has any defects.

2. The method according to claim 1, wherein step (a) further comprises:
   prior to step (b), mounting fourth and fifth ultrasonic transducers to the inspection unit for inspecting a root of the weld; and step (d) further comprises:
   placing the fourth and fifth ultrasonic transducers on opposite sides of the weld simultaneously with the second and third ultrasonic transducers, rotating the fourth and fifth ultrasonic transducers relative to the frame about the axis of the unit and simultaneously causing each of the fourth and fifth ultrasonic transducers to emit an acoustical signal and receive an acoustical signal from a root of the weld to determine if the root of the weld has any defects.

3. The method according to claim 2, wherein the fourth and fifth ultrasonic transducers are rotated simultaneously with the second and third ultrasonic transducers.

4. The method according to claim 1, further comprising stopping movement of the inspection unit along the pipe while performing step (c).

5. The method according to claim 1, wherein step (c) further comprises:
   predetermining a plurality of inspection areas at selected lineal increments along the pipe and a plurality of inspection sites circumferentially around the pipe at each inspection area;
   stopping movement along the pipe at each inspection area, then rotating the inspection unit relative to the frame about the axis of the frame; and
   automatically collecting the data at each inspection site while the inspection unit is rotated.

6. The method according to claim 1, wherein step (d) comprises rotating the second and third ultrasonic transducers less than one full revolution in one direction at a first weld, then rotating the second and third ultrasonic transducers back less than one full revolution in the opposite direction at a next weld.

7. The method according to claim 1, wherein the unit is stopped from movement along the pipe and the second and third ultrasonic transducers rotated less than one full revolution while step (d) is being performed.

8. A method of inspecting a pipe, comprising:
(a) providing a self-propelled drive unit having a longitudinal axis;
(b) mounting an inspection unit on the drive unit for rotation about the longitudinal axis, the inspection unit having a first ultrasonic transducer for determining a wall thickness of a pipe, second and third ultrasonic transducers spaced axially from the first ultrasonic transducer for detecting any flaws in a volume of a weld, and fourth and fifth ultrasonic transducers for detecting flaws in a root of the weld, the fourth and fifth ultrasonic transducers being spaced the same axial distances from the first ultrasonic transducer as the second and third ultrasonic transducers, but circumferentially offset, each of the transducers being mounted to a separate shoe that is movable between a retracted position and an extended position;
(c) stopping the unit within the pipe in a position that places the second and third ultrasonic transducers on opposite sides of a weld and the fourth and fifth ultrasonic transducers on opposite sides of the weld, causing the shoes that contain the second through fifth ultrasonic transducers to contact an inner diameter of the pipe, then rotating the inspection unit less than one full revolution; and
(d) while rotating the inspection unit, causing the second ultrasonic transducer to emit an acoustical signal into the volume of the weld and receiving a return acoustical signal with the third ultrasonic transducer to inspect the volume of the weld; and
(e) at the same time as step (e), causing the fourth ultrasonic transducer to emit an acoustical signal that reflects into the root of the weld, and receiving with the fourth ultrasonic transducers any acoustical signals resulting from any defects in the root of the weld, and causing the fifth ultrasonic transducer to emit an acoustical signal that reflects into the root of the weld and receiving with the fifth ultrasonic transducer any acoustical signals resulting from any defects in the root of the weld; and
(f) moving the inspection unit linearly within the pipe, moving the shoe containing the first ultrasonic transducer to an extended position in contact with the inner diameter of the pipe and causing the first ultrasonic transducer to periodically emit an acoustical signal into the pipe and detecting a return acoustical signal to determine wall thickness.

9. The method according to claim 8, wherein step (f) is performed at selected inspection areas along the pipe, and comprises stopping the inspection unit at the selected inspection areas and rotating the inspection unit at each inspection area less than one full revolution.

10. The method according to claim 9, further comprising preprogramming a selected number of inspection sites around a circumference of the pipe at each inspection area, and without stopping rotation of the inspection unit, automatically computing a wall thickness when the first transducer passes each of the inspection sites.

11. The method according to claim 8, further comprising placing the first ultrasonic transducer in a retracted position while performing steps (c)–(e) and the placing the second through fifth transducers in retracted positions while performing step (f).

12. The method according to claim 8, wherein step (b) further comprises mounting each of the transducers within a recess of a shoe, steps (c)–(e) further comprise flowing a liquid through each recess containing the second through fifth ultrasonic transducers, and step (f) further comprises flowing a liquid through the recess containing the first ultrasonic transducer.

13. An apparatus for inspecting pipe, comprising:
an inspection unit having an axis;
a first ultrasonic transducer carried by the inspection unit for emitting and receiving acoustical signals to determine a wall thickness of the pipe;
second and third ultrasonic transducers carried by the inspection unit along with the first ultrasonic transducer for emitting and receiving acoustical signals through a volume of a weld in the pipe;
fourth and fifth ultrasonic transducers carried by the inspection unit along with the first, second and third ultrasonic transducers, each for emitting acoustical signals and receiving acoustical signals that pass through a root portion of the weld; and
the second through fifth ultrasonic transducers being mounted for selective rotation about the axis of the inspection unit no more than one full revolution while emitting acoustical signals into and receiving acoustical signals from the weld.

14. The apparatus according to claim 13, further comprising a plurality of shoes to which the transducers are mounted, the shoes being urged radially outward from the axis for engaging an inner diameter of a pipe.

15. The apparatus according to claim 14, further comprising a plurality of recesses in outer surfaces of the shoes into which the transducers are mounted; and
a plurality of passages for delivering a coupling liquid to the recesses.

16. The apparatus according to claim 13, further comprising a plurality of shoes that are movable independently of each other in radial directions, each of the transducers being mounted to one of the shoes, the shoes being urged radially outward from the axis for engaging an inner diameter of a pipe.

17. An apparatus for inspecting pipe, comprising:
an inspection unit having an axis;
a first ultrasonic transducer carried by the inspection unit for emitting and receiving acoustical signals to determine a wall thickness of the pipe;
second and third ultrasonic transducers carried by the inspection unit for emitting and receiving acoustical signals through a volume of a weld in the pipe;
fourth and fifth ultrasonic transducers carried by the inspection unit, each for emitting acoustical signals and receiving acoustical signals that pass through a root portion of the weld; and
the second through fifth ultrasonic transducers being mounted for selective rotation about the axis of the inspection unit no more than one full revolution while emitting acoustical signals into and receiving acoustical signals from the weld;
a plurality of shoes that are movable independently of each other in radial directions, each of the transducers being mounted to one of the shoes, the shoes being urged radially outward from the axis for engaging an inner diameter of a pipe;
a pneumatic cylinder mounted to each of the shoes; and
a first valve that selectively causes the pneumatic cylinders to move the shoe containing the first ultrasonic transducer between retracted and extended positions; and a second valve that operates independently of the first valve for moving the shoes containing the second through fifth transducers between retracted and extended positions.

18. The apparatus according to claim 13, further comprising:
a drive unit onto which the inspection unit is mounted, the drive unit having a motor, a set of drive wheels driven by the motor and a set of support wheels that are spaced from the drive wheels and which freewheel; and
an encoder operatively coupled to the support wheels for providing an indication of linear travel of the unit along the pipe in response to rolling movement of the support wheels.

19. The apparatus according to claim 13, wherein the first transducer is also mounted for rotation about an axis of the inspection unit less than one full revolution, and the apparatus further comprises:
a rotational sensor mounted to the apparatus for providing an azimuth indication of the inspection unit as it rotates; and
a controller connected to the drive unit and the rotational sensor, the controller having a pre-programmable selector for selecting inspection sites spaced selected degrees apart around the circumference of the pipe, the controller automatically collecting data from the first ultrasonic transducer upon passing each inspection site.

20. An apparatus for inspecting pipe, comprising:
a frame having an axis and mounted on a set of drive wheels and a set of support wheels spaced axially from the drive wheels;
a linear drive motor mounted to the frame and coupled to the drive wheels for moving the frame linearly along an interior of a pipe;
an inspection unit mounted to the frame;
a radial drive motor for rotating the inspection unit relative to the frame about an axis of the frame;
a plurality of sets of shoes carried by the inspection unit and spaced circumferentially around the axis, each of the sets comprising at least two shoes spaced circumferentially apart from each other, the shoes within each of the sets being at the same axial position along the inspection unit, some of the sets being located at different axial positions from other of the sets;
a plurality of pneumatic cylinders, each mounted to one of the shoes of the inspection unit perpendicular to the axis;
at least one control valve coupled to the pneumatic cylinders for selectively moving the shoes radially outward to an extended position for engaging an inner diameter of the pipe and moving the shoes radially inward to a retracted position to facilitate entry of the inspection unit into the pipe;
a plurality of recesses in outer surfaces of the shoes;
a plurality of ultrasonic transducers mounted in the recesses for emitting and receiving acoustical pulses to determine a wall thickness of the pipe and detect defects in welds; and
a plurality of passages in the shoes for delivering a coupling liquid to the recesses.

21. The apparatus according to claim 20 wherein the support wheels rotate freely; and wherein the apparatus further comprises:
an encoder operatively coupled to the support wheels for providing an indication of linear travel of the unit along the pipe in response to movement of the support wheels.

22. The apparatus according to claim 20, wherein the inspection unit is cantilever mounted to one end of the frame.

23. The apparatus according to claim 20, wherein said at least one control valve comprises two control valves, one of the control valves controlling some of the pneumatic cylinders independently of the other control valve to enable some of the shoes to be in the retracted position while others are in the extended position.

24. An apparatus for inspecting pipe, comprising:
an elongated frame having an axis and mounted on at least two sets of wheels;
an inspection unit mounted to the frame intermediate forward and rearward ends of the frame, defining a forward frame portion and a rearward frame portion, with one of the sets of the wheels mounted to the forward portion and the other of the sets of wheels mounted to the rearward portion for rolling the frame horizontally along a pipe;
a radial drive motor for rotating the inspection unit relative to the frame about the axis of the frame;
a plurality of shoes spaced circumferentially around the axis, each of the shoes being elongated in an axial direction and urged radially outward relative to the inspection unit;
a plurality of recesses in an outer surface of each of the shoes;
a plurality of ultrasonic transducers mounted in the recesses for emitting and receiving acoustical pulses to determine a wall thickness of the pipe and detect defects in welds; and
a plurality of passages in the shoes for delivering a coupling liquid to the recesses.

25. An apparatus for inspecting pipe, comprising:
an elongated frame having an axis and mounted on at least two sets of wheels;
an inspection unit mounted to the frame intermediate forward and rearward ends of the frame, defining a forward frame portion and a rearward frame portion, with one of the sets of the wheels mounted to the forward portion and the other of the sets of wheels mounted to the rearward portion;
a radial drive motor for rotating the inspection unit relative to the frame about the axis of the frame;
a plurality of shoes spaced circumferentially around the axis, each of the shoes being elongated in a axial direction and urged radially outward relative to the inspection unit;
a plurality of recesses in an outer surface of each of the shoes;
a plurality of ultrasonic transducers mounted in the recesses for emitting and receiving acoustical pulses to determine a wall thickness of the pipe and detect defects in welds;
a plurality of passages in the shoes for delivering a coupling liquid to the recesses; and
wherein the shoes are urged radially outward by springs.

26. The apparatus according to claim 24 further comprising an encoder operatively coupled to the wheels for providing an indication of linear travel of the unit along the pipe in response to movement of the wheels.

27. An apparatus for inspecting pipe, comprising:
a frame mounted on wheels;
an inspection unit mounted to the frame;

a radial drive motor for rotating the inspection unit relative to the frame about the longitudinal axis of the frame;

a plurality of shoes carried by the inspection unit;

a plurality of recesses in outer surfaces of the shoes;

a plurality of passages in the shoes for delivering a coupling liquid to the recesses;

a first ultrasonic transducer carried by a first one of the shoes for emitting and receiving acoustical signals to determine a wall thickness of the pipe; and second and third ultrasonic transducers carried by second and third ones of the shoes while the first one of the shoes is carrying the first ultrasonic transducer, for emitting and receiving acoustical signals through a volume of a weld in the pipe, the second and third shoes being axially spaced apart from each other for location on opposite sides of a weld.

* * * * *